(12) United States Patent
Thieuleux et al.

(10) Patent No.: US 9,518,071 B2
(45) Date of Patent: Dec. 13, 2016

(54) HYDROSILYLATION METHOD

(71) Applicants: BLUESTAR SILICONES France SAS (50 Percent Part Interest), Lyons (FR); Universite Claude Bernard Lyon 1 (50 Percent Part Interest), Villeurbanne (FR)

(72) Inventors: Chloe Thieuleux, Villeurbanne (FR); Reine Sayah El Rayes, Villeurbanne (FR); Marie-Line Zanota, Villeurbanne (FR); Valerie Meille, Lyons (FR); Richard Vivier, Clermont Ferrand (FR); Sebastien Marrot, Lyons (FR)

(73) Assignees: BLUESTAR SILICONES FRANCE SAS, Lyons (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 5 days.

(21) Appl. No.: 14/653,069

(22) PCT Filed: Dec. 20, 2013

(86) PCT No.: PCT/EP2013/077581
§ 371 (c)(1),
(2) Date: Jun. 17, 2015

(87) PCT Pub. No.: WO2014/096306
PCT Pub. Date: Jun. 26, 2014

(65) Prior Publication Data
US 2015/0322095 A1    Nov. 12, 2015

(30) Foreign Application Priority Data
Dec. 21, 2012   (FR) .................... 12 62643

(51) Int. Cl.
| | | |
|---|---|---|
| C07F 7/08 | (2006.01) |
| B01J 19/24 | (2006.01) |
| B01J 37/03 | (2006.01) |
| B01J 21/08 | (2006.01) |
| B01J 23/42 | (2006.01) |
| B01J 29/03 | (2006.01) |
| B01J 35/00 | (2006.01) |
| B01J 37/02 | (2006.01) |

(52) U.S. Cl.
CPC .............. *C07F 7/0849* (2013.01); *B01J 19/24* (2013.01); *B01J 21/08* (2013.01); *B01J 23/42* (2013.01); *B01J 29/0325* (2013.01); *B01J 35/0013* (2013.01); *B01J 37/0203* (2013.01); *B01J 37/0211* (2013.01); *B01J 37/033* (2013.01); *B01J 37/036* (2013.01); *B01J 2219/24* (2013.01)

(58) Field of Classification Search
CPC ...... C07F 7/0849; B01J 19/24; B01J 2219/24; B01J 35/0013; B01J 37/033; B01J 37/0203; B01J 29/0325; B01J 37/036; B01J 37/0211; B01J 21/08; B01J 23/42
USPC ......................................... 556/456; 422/222
See application file for complete search history.

(56) References Cited

U.S. PATENT DOCUMENTS

| | | | |
|---|---|---|---|
| 7,038,001 B2 | 5/2006 | Breunig et al. | |
| 2009/0286899 A1 | 11/2009 | Hofmann et al. | |
| 2011/0257006 A1* | 10/2011 | Thieuleux ............ | B01J 29/0308 502/239 |

FOREIGN PATENT DOCUMENTS

WO    2010/040926    4/2010

OTHER PUBLICATIONS

International Search Report dated Jul. 1, 2014, corresponding to PCT/EP2013/077581.
M. Boualleg, et al.; "Selective and Regular Localization of Acessible PT Nanoparticles Inside the Walls of an Ordered Silica: Application as a Highly Active and Well-Defined Heterogeneous Catalyst for Propene and Styrene Hydrogenation Reactions"; Journal of Catalysis, vol. 284, No. 2; Dec. 1, 2011; pp. 184-193.

* cited by examiner

*Primary Examiner* — Porfirio Nazario Gonzalez
(74) *Attorney, Agent, or Firm* — Young & Thompson

(57) ABSTRACT

A method (P) for hydrosilylating at least one compound (C), including at least one unsaturation in the presence of an organosilicon compound (O) including at least one hydrogen atom per molecule bonded directly to a silicon atom, and of a catalytic hydrosilylation system including a structured porous material (A) including pores and an inorganic structure consisting of silicon oxide walls, in which metal nanoparticles are contained.

19 Claims, 1 Drawing Sheet

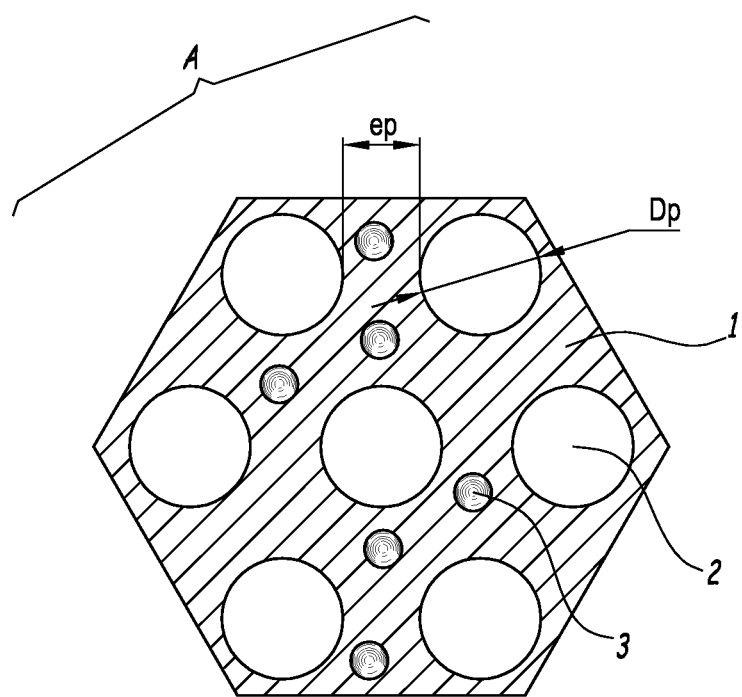

HYDROSILYLATION METHOD

FIELD OF THE INVENTION

The present invention relates to a novel hydrosilylation method applying a heterogeneous catalyst and to a device allowing application of said method.

BACKGROUND OF THE INVENTION

Hydrosilylation reactions of at least one compound (C) comprising at least one unsaturation in the presence of an organosilicon compound (O) comprising at least one hydrogen atom directly bound to a silicon atom (either at least one Si—H group or a hydrogen siloxane function) are considerably widespread in the silicone industry for accessing silanes and functionalized polysiloxanes and also for preparing silicone lattices obtained by cross-linking between polymethylhydrogen siloxanes and polymethylvinylsiloxane oils. These reactions are generally catalyzed by organometal complexes based on platinum according to a homogenous catalysis mechanism. Among the well known homogenous hydrosilylation catalysts, mention may be made of Karstedt's platinum of formula $Pt_2(DVTMS)_3$, wherein DVTMS represents divinyltetramethyldisiloxane. However, this type of catalyst has different drawbacks. On the one hand, it is relatively unstable and changes during the reaction by forming colloidal species of Pt(0), the size of which is not controlled, which lead to a coloration of the reaction medium and obtained oils ranging from yellow to black. On the other hand, the steps for removing the platinum are costly and the catalyst cannot be recycled. Therefore, there exists a benefit to access easily recyclable, performing, heterogeneous catalysts, for which the preparation, the application and the activity are reproducible, giving the possibility of continuously operating for hydrosilylation reactions.

Heterogeneous catalysts, notably based on platinum, for the hydrosilylation reaction are for example known from U.S. Pat. No. 7,038,001.

However, a non-negligible amount of the platinum, contained in these heterogeneous catalysts, may be sorted out and solubilized in the reaction medium, this is then referred to as platinum in a homogenous phase. This phenomenon has different drawbacks:
  the solubilization of a portion of the platinum of the catalyst induces a variability of the activity of the catalyst and therefore problems of reproducibility of hydrosilylation reactions;
  in the case of partial hydrosilylation, i.e. when the reaction medium at the end of the reaction still comprises compounds comprising at least one hydrogen atom directly bound to at least one silicone atom, the platinum which was solubilized in the reaction medium may catalyze secondary reactions when said reaction medium is left in air. This may notably be a dehydrogenation condensation reaction between the SiH units and water from air, this reaction is at the origin of gelling of the surface of the reaction medium and of evolvement of dihydrogen with the notable risks of explosion which ensue. Sorting out platinum in the reaction medium therefore generates stability problems upon storage and of safety of the media comprising Si—H groups.

In order to limit sorting out of the metal nanoparticles in a homogenous phase in the reaction medium, it is known from the prior art how to have the catalyst before use be subject to a heat treatment step under a controlled atmosphere. However, this heat treatment step generally has the effect of reducing the catalytic activity of the catalyst.

Therefore there exists a benefit of providing a method for hydrosilylation of compounds comprising at least one unsaturation and of organosiloxane compounds applying a catalytic system in which metal nanoparticles are sufficiently supported, while remaining accessible to the reagents, so as not to be sorted out in a homogenous phase in the reaction medium.

SUMMARY OF THE INVENTION

The object of the present invention is therefore to provide a hydrosilylation method applying a stable heterogeneous catalytic system having low or even nil leaching and being reproducible.

The object of the invention is also to provide a hydrosilylation method which may be continuously applied.

Another object of the invention is to provide a hydrosilylation method allowing significant versatility of the obtained products, notably giving the possibility of carrying out partial hydrosilylations.

Another object of the invention is also to provide a hydrosilylation method requiring limited amounts of metal nanoparticles.

The object of the invention is also to provide a device allowing application of this method, notably a device allowing continuous application of the method of the invention.

Other objects will become apparent in the light of the description of the invention which follows.

DETAILED DESCRIPTION OF THE INVENTION

The present invention relates to a method (P) for hydrosilylating at least one compound (C) comprising at least one unsaturation in the presence of an organosilicon compound (O) comprising at least one hydrogen atom directly bound to a silicon atom (i.e. at least one Si—H group also called a hydrogen siloxane function) and a hydrosilylation catalytic system comprising a structured porous material (A) including pores and an inorganic backbone consisting of silicon oxide walls in which metal nanoparticles are contained.

In the subsequent discussion, the expressions <<structured material (A)>> or <<material (A)>> are used in an equivalent way for designating the structured porous material (A) including pores and an inorganic backbone consisting of silicon oxide walls in which metal nanoparticles are contained.

In the compound comprising an unsaturation, the unsaturation may consist in an ethylenic double bond or in an acetylenic triple bond.

The compound (C) according to the invention is a chemical compound comprising at least one unsaturation preferably not being part of an aromatic ring. The compound (C) notably comprises at least one alkene function and/or an alkyne function. Any compound comprising at least one alkene function and/or one alkyne function may be used in the method according to the invention, insofar that it does not contain any reactive chemical function which may interfere or even prevent the hydrosilylation reaction.

According to an embodiment, the compound (C) comprises one or several alkene functions and from 2 to 40 carbon atoms. It may further comprise 1 to 20 heteroatoms selected from N, P, O, S, F, Cl, Br and I. When the compound (C) comprises several alkene functions, the latter may be conjugate or not.

According to another embodiment, the compound (C) comprises one or several alkyne functions and from 2 to 40 carbon atoms. It may further comprise 1 to 20 heteroatoms selected from N, P, O, S, F, Cl, Br and I. When the compound (C) comprises several alkyne functions, the latter may either be conjugated or not.

The compound (C) may be selected from the compounds of formula (I) or (II):

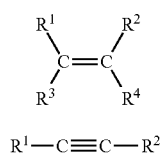

(I)

$$R^1-C\equiv C-R^2$$ (II)

wherein:
$R^1$, $R^2$, $R^3$ and $R^4$ represent, independently of each other,
 a hydrogen atom;
 a halogen atom selected from fluorine, chlorine, bromine and iodine;
 an alkyl group;
 an cycloalkyl group;
 an aryl group;
 a heteroaryl group;
 a heterocycloalkyl group;
 an alkoxy group;
 an aryloxy group;
 a cycloalkoxy group;
 an alkylsilyl group;
 an alkoxysilyl group;
 a carboxylic acid group;
 an alkyl ester group;
 a urea group;
 an amide group;
 a sulfonamide group;
 an imide group;
 a cyano group;
 an aldehyde group;
 an alchol group;
 a thiol group;
 an amine group;
 an imine group;
 a sulfide group;
 a sulfoxide group;
 a sulfone group;
 an azide group;
 an allyl phosphonate group; or
 an allyl phosphate group;
these groups may themselves be substituted on their alkyl and/or cycloalkyl and/or aryl portion(s) with:
 one or several $C_1$-$C_8$ alkyl groups, optionally halogenated;
 one or several $C_1$-$C_8$ alkoxy groups, optionally halogenated;
 one or several aryl groups, optionally halogenated;
 one or several halogen atom;
 one or several carboxylic acid groups;
 one or several ester groups;
 one or several ether groups;
 one or several urea groups;
 one or several amide groups;
 one or several sulfonamide groups;
 one or several imide groups;
 one or several cyano groups;
 one or several aldehyde groups;
 one or several ketone functions;
 one or several alcohol groups;
 one or several thiol groups;
 one or several amine groups;
 one or several imine groups;
 one or several sulfide groups;
 one or several sulfoxide groups;
 one or several sulfone groups;
 one or several azide groups;
 one or several phosphate groups; and/or
 one or several phosphonate groups;
 or
at least two groups selected from $R^1$, $R^2$, $R^3$ and $R^4$ form together with the carbon atoms to which they are bound one or several cycloalkyl, heterocycloalkyl, aryl or heteroaryl groups, these cycloalkyl, heterocycloalkyl, aryl and heteroaryl groups may be substituted with one or several $C_1$-$C_8$ alkyl groups, optionally halogenated; with one or several $C_1$-$C_8$ alkoxy groups, optionally halogenated; with one or several aryl groups, optionally halogenated; with one or several halogen atoms; with one or several carboxylic acid groups; with one or several ester groups; with one or several ether groups, with one or several urea groups; with one or several amide groups; with one or several sulfonamide groups; with one or several imide groups; with one or several cyano groups; with one or several aldehyde groups; with one or several ketone functions; with one or several alcohol groups; with one or several thiol groups; with one or several amine groups; with one or several imine groups; with one or several sulfide groups; with one or several sulfoxide groups; with one or several sulfone groups; with one or several azide groups; with one or several phosphate groups; and/or with one or several phosphonate groups;
the remaining groups from among $R^1$, $R^2$, $R^3$ and $R^4$ being as defined earlier, and mixtures thereof.

Preferably, $R^1$, $R^2$, $R^3$ and $R^4$ represent independently of each other:
 a hydrogen atom;
 a $C_1$-$C_{16}$ alkyl group, optionally substituted with a hydroxy group or a halogen atom;
 a phenyl, optionally substituted with a $C_1$-$C_4$ alkyl group, with a halogen, with a $C_1$-$C_4$ alkyl group itself substituted with one or several halogens, with a $C_1$-$C_4$ alkoxy group or with an amine function optionally substituted once or twice with a $C_1$-$C_4$ alkyl group;
 a pyridine;
 a $C_1$-$C_8$ alkyl ester;
 a cyano function;
 a carboxylic acid function;
 a $C_1$-$C_4$ acyloxy group, notably acetyloxy;
 a primary amide group, notably non-substituted on the nitrogen or substituted once or twice with a $C_1$-$C_4$ alkyl group;
 a polyethoxylated alkyl group, optionally substituted with a hydroxy or a ketone.

Advantageously, $R^1$ may be a hydrogen atom, and $R^3$ may represent a substituent different from a hydrogen atom. In the case of a compound of formula (I), $R^2$ and $R^4$ may further be hydrogen atoms.

Preferably, the compound (C) may also be selected from the group consisting of:
 $C_1$-$C_4$ alkyl acrylates and methacrylates;
 acrylic acid or methacrylic acid;

acetylene;

alkenes, preferably octene and more preferentially 1-octene;

non-conjugate dienes and preferably hexadiene or octadiene;

allyl alcohol;

allylamine;

allyl and glycidyl ether;

allyl and piperidine ether and preferably sterically hindered allyl and piperidine ether;

styrene and preferably alpha-methyl-styrene;

1,2-epoxy-4-vinylcyclohexane;

chlorinated alkenes and preferably allyl chloride;

fluorinated alkenes and preferably 4,4,5,5,6,6,7,7,7-nonafluoro-1-heptene, and mixtures thereof.

The compound (C) may also be selected from compounds comprising several alkene functions, preferably two or three alkene functions, and more preferably selected from the following compounds:

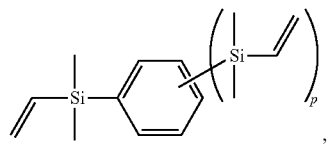

with p having the value 1 or 2,

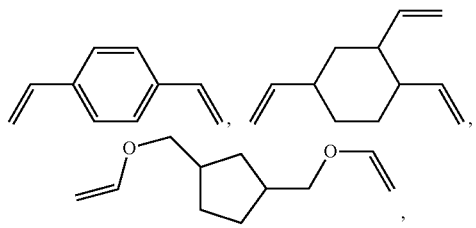

and mixtures thereof.

It is also possible within the scope of the invention to have a mixture of the aforementioned compounds (C) comprising an alkene function and of the aforementioned compounds (C) comprising several alkene functions.

The compound (C) may therefore also comprise chemical functions which will allow chemical modification of the compound obtained subsequently to the hydrosilylation reaction.

The hydrosilylation of compounds comprising both one or several ethylenic double bonds and one or several acetylenic triple bonds is also contemplated within the scope of the invention.

Within the scope of the present invention, the organosilicon compound (O) comprises at least one hydrogen atom directly bound to a silicon atom (i.e. at least one Si—H group).

Preferably, the silicon atoms of the compounds (O) are bound to at most one hydrogen atom.

The compound (O) may be a silane compound or a siloxane compound, notably a hydrogen silane or a polyorganosiloxane.

By <<hydrogen silane>> compound, in the present invention, are meant chemical compounds belonging to the group of silanes, therefore comprising at least one silicon atom, and at least comprising a hydrogen atom bound to the silicon atom. Preferably, the hydrogen silane compound according to the invention comprises less than 5 silicon atoms.

Any hydrogen silane compound may be used in the method according to the invention, insofar that it does not contain any reactive chemical function which may interfere with, or even prevent the hydrosilylation reaction.

According to an embodiment of the present invention, the hydrogen silane compound may be selected from among the compounds of formula (III):

wherein:

R represents, independently of the others, a hydrogen atom; a halogen atom, preferably chlorine; an alkyl group optionally substituted with one or several aryl or cycloalkyl groups, with one or several halogen atoms and/or with one or several ketone functions; a cycloalkyl group optionally substituted with one or several alkyl groups and/or with one or several halogen atoms; or an aryl group optionally substituted with one or several alkyl groups and/or with one or several halogen atoms;

R' represents, independently of the others, an alkyl group optionally substituted with one or several aryl or cycloalkyl groups, with one or several halogen atoms and/or with one ketone function; a cycloalkyl group optionally substituted with one or several alkyl groups and/or with one or several halogen atoms; or an aryl group optionally substituted with one or several alkyl groups and/or with one or several halogen atoms;

R" represents, independently of the others, a hydrogen atom; a halogen atom, preferably chlorine; an alkyl group optionally substituted with one or several aryl or cycloalkyl groups and/or with one or several halogen atoms; a cycloalkyl group optionally substituted with one or several alkyl groups and/or with one or several halogen atoms; or an aryl group optionally substituted with one or several alkyl groups and/or with one or several halogen atoms; and m, n and o are integers of value 0, 1, 2 or 3, and m+n+o=3, R, R' and R" being identical or different, and mixtures thereof.

The hydrogen silane compound may be selected from among the compounds of formula (III) wherein the symbols m=0, n=0 and o=3, and R" represents a hydrogen atom, a halogen atom, preferably chlorine, a linear or branched $C_1$-$C_8$ alkyl group or an aryl group.

The hydrogen silane compound may in particular be tris(trimethylsilyl)silane.

Alternatively, the hydrogen silane compound may be selected from among the compounds of formula (III) wherein the symbols m=3, n=0 and o=0, and R represents a hydrogen atom, a halogen atom, preferably chlorine, a linear or branched $C_1$-$C_8$ alkyl group or an aryl group.

The organosilicon compound (O) may also be a polyorganosiloxane comprising:
(i) at least one siloxyl unit of formula (IV)

$$H_d Z^3_e SiO_{\frac{4-(d+e)}{2}} \quad (IV)$$

wherein:
d=1 or 2, preferably d=1,
e=0, 1 or 2
d+e=1, 2 or 3,
the symbol(s) $Z^3$, either identical or different, represent a monovalent hydrocarbon group notably having from 1 to 30 carbon atoms optionally substituted with heteroatoms or radicals comprising heteroatoms and preferably selected from the group formed by alkyl groups having from 1 to 8 carbon atoms inclusive and aryl groups, and further more preferentially selected from the group formed by a methyl, ethyl, propyl, 3,3,3-trifluoropropyl, xylyl, tolyl and phenyl radical, preferably methyl or phenyl, for example methyl; and
(ii) optionally at least one siloxyl unit of formula (V)

$$Z^2_c SiO_{\frac{4-c}{2}} \quad (V)$$

wherein:
c=0, 1, 2 or 3, preferably 1, 2 or 3;
the symbol(s) $Z^2$, either identical or different, represent a monovalent hydrocarbon group notably having from 1 to 30 carbon atoms optionally substituted with heteroatoms or radicals comprising heteroatoms and preferably selected from the group formed by alkyl groups having from 1 to 8 carbon atoms inclusive and aryl groups, and further more preferentially selected from the group formed by a methyl, ethyl, propyl, 3,3,3-trifluoropropyl, xylyl, tolyl and phenyl radical, preferably methyl or phenyl, for example methyl.

The polyorganosiloxane may have a cyclic branched, linear structure or a networked structure.

These linear polyorganosiloxanes may be oils having a dynamic viscosity of 25° C. comprised between 1 mPa·s and 100,000 mPa·s, preferentially between 10 mPa·s and 5,000 mPa·s, or gums having a dynamic viscosity at 25° C. of more than 100,000 mPa·s.

All the viscosities mentioned in the present discussion correspond to a so-called <<Newtonian>> dynamic viscosity quantity at 25° C., i.e. the dynamic viscosity which is measured, in a way known per se, at a sufficiently low shear velocity gradient so that the measured viscosity is independent of the velocity gradient.

Examples of polyorganosiloxanes which may be compounds (O) are:
dimethylpolysiloxanes with hydrogen dimethylsilyl ends;
dimethyl hydrogen methylpolysiloxanes with trimethylsilyl ends;
dimethyl hydrogen methylpolysiloxanes with hydrogen dimethylsilyl ends;
hydrogen methylpolysiloxanes with trimethylsilyl ends; or
cyclic hydrogen methylpolysiloxanes;
and mixtures thereof.

By <<alkyl>>, is meant a linear or branched hydrocarbon chain comprising from 1 to 40 carbon atoms, preferably from 1 to 20 carbon atoms, more preferentially from 1 to 10 carbon atoms. An alkyl group may be selected from the group formed by methyl, ethyl, isopropyl, n-propyl, tert-butyl, isobutyl, n-butyl, n-pentyl, isoamyl and 1,1-dimethylpropyl.

By <<cycloalkyl>> according to the invention is meant a monocyclic or polycyclic saturated hydrocarbon group, preferably monocyclic or bicyclic, containing from 3 to 20 carbon atoms, preferably from 5 to 8 carbon atoms. When the cycloalkyl group is polycyclic, the multiple cyclic rings may be attached to each other through a covalent bond and/or through a spinanic atom and/or be condensed together. A cycloalkyl group may be selected from the group formed by cyclopropyl, cyclobutyl, cyclopentyl, cyclohexyl, cycloheptyl, cyclooctyl, adamantane and norborane.

By <<aryl>>, according to the invention is meant an aromatic hydrocarbon group containing from 5 to 18 carbon atoms, either monocyclic or polycyclic. An aryl group may be selected from the group formed by phenyl, naphthyl, anthracenyl and phenanthryl.

By <<halogen atom>>, according to the invention is meant an atom selected from the group formed by fluorine, chlorine, bromine and iodine.

By <<heteroaryl>>, according to the invention is meant an aryl group in which at least on carbon atom has been substituted with a heteroatom selected from O, N, S and P. A heteroaryl group may be selected from the group formed by pyranyl, furanyl, pyridinyl, pyrimidinyl, pyrrolyl, pyrazolyl, imidazolyl, isothiazolyl, isoxazolyl and indolyl.

By <<heterocycloalkyl>>, according to the invention is meant a cycloalkyl group in which at least one carbon atom has been substituted with a heteroatom selected from O, N, S and P. Preferably the heterocycloalkyl comprises from 5 to 10 members. A heterocycloalkyl group may in particular be the monocyclic oxiranyl group or the bicyclic epoxycyclohexyl group.

By <<alkoxy>>, according to the invention is meant an alkyl group as defined herein before bound to an oxygen atom. An alkoxy group may be selected from the group formed by methoxy, ethoxy, propoxy and butoxy.

By <<aryloxy>>, according to the invention is meant an aryl group as defined hereinbefore, bound to an oxygen atom. An aryloxy group may for example be the phenoxy group.

By <<cycloalkoxy>>, according to the invention is meant a cycloalkyl group as defined hereinbefore, bound to an oxygen atom.

By <<alkylsilyl>>, according to the invention is meant an alkyl group as defined herein before bound to a silicon atom.

By <<alkoxysilyl>>, according to the invention is meant an alkoxy group as defined hereinbefore, bound to a silicon atom.

The catalyst of the invention comprises a structured porous material (A) including a structured inorganic backbone consisting of silicon oxide walls into which metal nanoparticles are incorporated.

Within the scope of the present invention, by "structured material" is meant a material which has an organized structure notably characterized by the presence of at least one diffraction peak in a small-angle x-ray powder diffractogram (small angle x-ray scattering (Glatter and Kratky, Academic Press London 1982)). The diffraction peak observed in a small-angle x-ray powder diffractogram obtained for a structured material is associated with a characteristic repetition distance of the relevant material. This repetition distance or <<spatial repetition period of the structured system>> corresponds to the periodicity of the pores within the material, in the case of porous materials. In the material (A) of the invention, the backbone is therefore structured, this is why one refers to walls and pores (FIG. 1).

The structuration of the final material (A), as determined by small angle x-ray diffraction or by microscopy, may be of the vermicular, lamellar, hexagonal (one dimension or two dimensions) or cubic type. Preferably, the structuration of the final material is hexagonal, preferably hexagonal in two dimensions.

The thickness (or width) of the walls (FIG. 1) of the material (A), notably determined by diffraction of X-rays at small angles and by nitrogen adsorption/desorption measurements, is notably greater than 3 nm, preferably from 5 to 15 nm. The thickness of the walls corresponds to the distance between two pores (ep in FIG. 1).

The size of the metal nanoparticles is preferably less than or equal to the width of the walls forming the inorganic backbone of the material (A). In this way, the nanoparticles may be totally integrated inside the walls thereby avoiding their sorting out in the reaction medium. Preferably, the metal nanoparticles present within the material (A) have a nanometric size, i.e. they have an average diameter from 1 to 10 nm, the average diameter being determined for example by transmission electron microscopy as a histogram of sizes or preferably by the wide angle X-ray diffraction technique (WAXS "wide angle x-ray scattering").

Within the scope of the present invention by metal nanoparticles are meant nanoparticles of metal in the zero oxidation state, also noted as M(0) or metal (0) (M representing the metal).

Preferably, within the scope of the invention, the metal which is the active catalytic species, is selected from platinum, rhodium, ruthenium, iridium, iron, copper and palladium, a mixture of two or more of these metals may also be contemplated. Preferably, the metal is platinum.

The metal nanoparticles are included in the walls of the material (A) and are therefore not salted out in a reaction medium like this may be the case for conventional heterogeneous catalysts.

The material (A) of the invention is preferably as a powder. Advantageously, these powders have a large specific surface area which gives the possibility of obtaining high catalytic activity. Further, the application, in the catalytic system, of a material (A) as a powder advantageously gives the possibility of being able to separate it from the reaction medium, for stopping the hydrosilylation reaction and/or for reuse. This separation may be achieved by filtration. It is also possible to deposit this powder on a substrate. This latter method is particularly indicated for conducting methods continuously.

Advantageously and preferably, the material (A) has double porosity. The mesopores of the material (A) preferably have a diameter from 2 to 50 nm, preferably from 5 to 30 nm, for example from 5 to 20 nm. The microporous channels, present in the walls of the material (A), preferably have a diameter of less than 2 nm, preferably from 0.5 to 2 nm. The size of the mesopores may be determined by any method known to one skilled in the art, notably by nitrogen adsorption/desorption at 196° C. (i.e. 77K) by the BJH (Barrett, Joyner and Halenda) method for example defined in the "Techniques de l'ingénieur", "Technique des matériaux pulvérulents ou poreux" (technique of powdery and porous materials). The size of the micropores may be determined by any method known to one skilled in the art and preferably by nitrogen adsorption/desorption at 196° C. by the <<t-method>> (<<t-plot>>) for example defined in "Techniques de l'ingénieur", "Technique des matériaux pulvérulents ou poreux".

Preferably, the structured material (A) has a BET specific surface area from 20 to 1,200 $m^2/g$, preferably from 300 to 1,100 $m^2/g$. The BET specific surface area is for example defined in "Techniques de l'ingénieur", "Technique des matériaux pulvérulents ou poreux".

Surprisingly, in spite of the reduced size of the microporous channels in the walls of the material (A), the latter give the possibility to the reagents (compounds (C) and compounds (O)) and notably to the organosilicon compounds of large molecular masses and viscosities of accessing the metal nanoparticles. Patent application WO2010/040926 specifies catalysts such as those described in the present invention comprising metal nanoparticles in the walls of an inorganic backbone allowing hydrogenation of styrene. However, styrene has a viscosity close to that of water and may therefore easily access the metal nanoparticles comprised in the walls of the constituent material of the catalyst. Also one skilled in the art might have expected that the organosilicon compounds, with larger sizes and viscosities, would block the pores of the material (A) and not have access to the metal nanoparticles.

The material (A) according to the invention may be deposited on a substrate in order to form a macro-structured catalytic system, the substrate may for example be metal beads, the walls of a reactor or walls of an element of a reactor (for example a mixer blade), etc. Deposition of the material (A) on the substrate may be accomplished by any method known to one skilled in the art and notably by the methods described in the publications of Pérez et al. (Chemical Engineering Journal, 2010, 158, 325-322), Zhao et al. (Catalysis Today, 2009, 147, 215-219) and Wei et al. (Catalysis Today, 2009, 147, 66-70). Preferably, after depositing the material (A) on the substrate (or the support), the obtained catalytic system is calcined in order to remove any traces of compounds which may block the pores of the material (A).

Advantageously, the material (A) comprises from 0.05 to 3% by weight of metal nanoparticles based on the total weight of the material (A), preferably from 0.1 to 1% by weight, for example from 0.1 to 0.5% by weight.

Preferably, in the method of the invention, the catalytic system may be applied many times without any loss of activity and without any leaching.

Advantageously, all the preferred and advantageous characteristics defining the catalyst may be combined with each other.

Although this is not necessary, the catalyst according to the invention may be treated by an $H_2$ flow before use.

Preferably, within the scope of the present invention, the material (A) may be obtained by the method described in patent application WO2010/040926 and in the publication of Boualleg et al. (Journal of Catalysis, 2011, 284, 184-193) to which one skilled in the art may refer and which are incorporated herein by reference.

Preferably, the material (A) of the invention is obtained by a method comprising the following steps:

a) having available a suspension of hydrophilic nanoparticles of a metal in the state of oxidation of zero stabilized by non-exchangeable ligands which give their hydrophilicity to the nanoparticles; and b) growing the inorganic backbone from an inorganic precursor of silicon oxide, around metal (0) nanoparticles stabilized by non-exchangeable ligands, in the presence of a porogenic agent; and c) removing the porogenic agent and at least partly the non-exchangeable ligands.

By <<non-exchangeable>> are notably meant that the ligands giving the hydrophilicity to the metal nanoparticles should not be exchanged with the porogenic agents. Indeed, such an exchange would have the effect of making the metal nanoparticles hydrophobic, the latter would then be placed in the pores of the material and not in the walls of the inorganic backbone.

Advantageously, the non-exchangeable nature of the ligands added to the fact that they make the metal nanoparticles hydrophilic allows said metal nanoparticles to be localized in the walls and not in the pores.

Advantageously, this method gives the possibility of growing the inorganic backbone of the catalyst directly around metal nanoparticles. This causes a regular distribution of the metal nanoparticles which are well spaced apart and distributed within the obtained material (A), which limits their sintering. The metal nanoparticles are thus stabilized by the inorganic backbone of the material (A).

As an example of non-exchangeable hydrophilic ligands giving their hydrophilicity to the metal nanoparticles, mention may be made of 3-chloropropylsilane, N-(3-trihydrogen silylpropyl)-imidazole, chlorobenzylsilane, chlorodimethylsilane, salts of N-(3-trihydrogen silylpropyl)alkylimidazolium or salts of N-(3-trihydrogen silylpropyl)aryl-imidazolium, N-(benzyltrihydrogen silyl)-imidazole, salts of N-(benzyltrihydrogen silyl)-alkylimidazolium or salts of N-(benzyltrihydrogen silyl)-arylimidazolium, and also salts of N-(benzyltrihydrogen silyl)trialkylammonium or dibutyl-4,7,10-trioxaundecylstannane, etc. The salts may be tin or germanium salts, preferably tin salts. Such ligands are commercial ligands, or may be prepared according to techniques well known to one skilled in the art. In the case of ligands comprising a tin or germanium atom, reference may be made to F Ferkous, Journal of Organometallic Chemistry, 1991, Volume 420, Issue 3, pages 315-320 and to P Riviere, Journal of Organometallic Chemistry, 49 (1973) 173-189.

The suspension of hydrophilic nanoparticles may be a colloidal suspension prepared according to techniques well known to one skilled in the art, notably from a metal(0) precursor, for example $Pt(dba)_2$ (dba=dibenzylidene acetone), Ru(COD)(COT) (COD=cyclooctadiene; COT=cyclooctatriene), which is put into the presence of non-exchangeable hydrophilic ligands in a conventional polar organic solvent (for example water, alcohol, THF, tetrahydrofurane, ether . . . ) or conventional apolar organic solvent (for example a saturated or unsaturated hydrocarbon), preferably THF. The synthesis of the metal nanoparticles is achieved under hydrogen pressure in the presence of a reducing agent (for example $NaBH_4$) advantageously with 0.2 to 5 equivalents of stabilizer ligands per atom of engaged metal.

The growth of the inorganic backbone of the material (A) is achieved by a sol-gel method (L. L. Hench et al., Chem. Rev., 1990, 33-72 and S. Biz et al., Catal. Rev.-Sci. Eng, 1998, 0(3), 329-407). The hydrolysis and the polycondensation of the silicon oxide precursor allows growth of the inorganic backbone.

Preferably, the growth of the inorganic backbone of the material (A) is achieved in an aqueous medium or in an aqueous mixture with at least one co-solvent of the alcohol type (for example a linear alcohol, notably butanol), of the ether type (for example THF) or dimethylformamide (DMF).

It is also possible to add a porogenic agent into this suspension.

The growth of the inorganic backbone of the material (A) will preferably be achieved with at least one of the following conditions, alone or preferably as a combination:
a temperature from 0 to 100° C., preferentially from 20 to 65° C.,
a (metal inorganic precursor)/(porogenic agent) ratio in moles from 30 to 300,
a (metal of the nanoparticles)/(metal of the inorganic precursor) weight ratio from 0.001 to 50% or further less than 10%, and preferably from 0.001 to 5% and preferentially from 0.005 to 5%, or further from 0.05 to 5%,
a pH from 0 to 10 and preferentially from 0 to 4,
in the presence of a hydrolysis-polycondensation catalyst of the acid type for example HCl, of the basic type, for example $NH_3$, KOH, NaOH or a nucleophilic type, for example NaF or TBAF.

The porogenic agent is preferably an amphiphilic compound of the surfactant type, notably a copolymer. The essential feature of this compound is that it is able to form micelles in the reaction mixture, so as to lead to a mineral matrix having an organized structure.

As a porogenic agent, mention may be made of (EO=ethylene oxide and PO=propylene oxide):
anionic templates, such as sodium dodecyl sulfate;
cationic templates such as ammonium salts and notably tetraalkylammonium salts like those of cetyltrialkylammonium or dodecyltrialkylammonium, imidazolium salts such as 1-hexadecane-3-methylimidazolium bromide, pyridinium salts such as n-hexadecylpyridinium chloride;
non-ionic templates, and notably amines, such as hexadecylamine or dodecylamine;
alkylpolyethylene or alkylarylpolyethylene oxides, such as Brij® 52 ($C_{16}H_{33}O(CH_2CH_2O)_2H$), Tergitol® 15-S-12 ($C_{11-15}H_{23-31}O(CH_2CH_2O)_{12}H$), Triton X® 25-100 ($C_{14}H_{22}O(C_2H_4O)_{n1}$ with n1=9 to 10), Montanox® 20 (Sorbitan.20EO.monooleyl ester), octylphenol-10 EO (p-$C_8H_{17}C_6H_4O(CH_2CH_2O)_{10}H$), lauryl ether-n EO ($C_{12}H_{25}O(CH_2CH_2O)_{n2}H$, with n2=2, 4, 8);
templates of the polysorbate type, such as Tween® 20 (IUPAC name: polyoxyethylene (20) sorbitan monolaurate) and 30;
copolymers with amphiphilic blocks, such as tri-block copolymers Pluronic® P123 ($EO_{20}$—$PO_{70}$-$EO_{20}$), Pluronic® F127 ($EO_{77}$—$PO_{29}$-$EO_{77}$) or Pluronic® F108 ($EO_{132}$—$PO_{50}$-$EO_{132}$);
polymers (either functional or not) and notably block polymers such as Pluronic® P123, Pluronic® F127 or F108 as mentioned earlier or further conventional polymers of the PE (polyethylene), PP (polypropylene), PMMA (methyl polymethacrylate), polystyrene type, etc.

Such porogenic agents have already been widely used in the prior art.

The removal of the porogenic agent and of the ligands may be accomplished with any method known to one skilled in the art, notably by calcination in air at 350° C. or by an iron/UV treatment which consists of suspending the obtained material in an aqueous solution of sulfuric acid, of adding a $FeSO_4$ solution and of mixing the solution obtained in air, at room temperature and under UV irradiation.

One skilled in the art, because of his/her general knowledge, may preferably select experimental conditions (nature and size of the porogenic agent, pH of a synthesis, (porogenic agent)/(mineral precursor) ratio, temperature, type of hydrolysis-polycondensation catalyst) in order to allow walls with sufficient thickness to be obtained in order to be able to insert the metal particles therein.

More preferably, the catalyst of the invention may be obtained by the method comprising the following steps:

i) preparing a colloidal solution of platinum consisting of placing under reduced pressure at room temperature, a precursor of metal nanoparticles, notably of Pt(0), for example Pt(dba)$_2$, and then adding an organic solvent for example THF and finally a non-exchangeable hydrophilic ligand, preferably 3-chloropropylsilane, in solution in an organic solvent, for example THF, the obtained mixture is stirred, optionally under hydrogen pressure notably when the platinum precursor is not easily reducible or if a lack of ligand is applied;

ii) preparing a homogeneous solution by mixing a porogenic agent, for example Pluronic 123 ®, in water in the presence of NaF;

iii) adding into the solution obtained in step ii) the colloidal solution of step i) and intensive stirring;

iv) evaporating the organic solvents from the solution obtained in step iii);

v) preparing a solution by mixing TEOS (tetraethylorthosilicate) and an aqueous acid solution for example HCl down to a final pH of about 1.5;

vi) mixing the solutions obtained in steps iv) and v) and stirring at a temperature comprised between 20 and 40° C.;

vii) filtering the solution of step vi) and washing the obtained solid successively with water, ethanol, acetone and ether;

viii) removing the porogenic agent and the ligands by calcination at 350° C. or by treating in water at an acid pH under UV in the presence of iron (II) or iron (III) salts.

The TEOS in an acid solution is pre-hydrolyzed (step v) and then condensation is accomplished by adding NaF in the presence of the metal nanoparticles (step vi). Both of these steps allow growth of the inorganic backbone.

The hydrosilylation method according to the present invention may be conducted at a temperature from 15 to 150° C., preferably from 20 to 100° C., for example from 30 to 80° C.

The hydrosilylation method according to the invention may be applied in air or under an inert atmosphere, for example under a nitrogen atmosphere.

Generally, the hydrosilylation reaction may be achieved in a solvent or in the absence of solvent. Alternatively, one of the reagents may play the role of a solvent, this may for example be the case of the compounds (C). Suitable solvents are those which are miscible with the organosilicon compound. Examples of particular solvents are aliphatic hydrocarbons, for example pentane, hexane, heptane, pentamethylheptane or petroleum distillation fractions; aromatic hydrocarbons, for example benzene, toluene, xylene (ortho-, para- and meta-xylene); halogenated aliphatic or aromatic hydrocarbons, for example tetrachloroethylene; or ethers, for example tetrahydrofurane or dioxane.

Preferably, in the method of the invention, the amount of metal nanoparticles applied based on the total weight of the compounds (C) and (O) (the reagents) is from 1 to 50 ppm, preferably from 5 to 20 ppm.

Advantageously, the relative amount of compound (C) and of compound (O) may be controlled.

The molar ratio $$R = \frac{\text{number of unsaturations of the } C \text{ compounds}}{\text{number of } SiH \text{ groups of the } O \text{ compounds}}$$

may vary from 1:100 to 25:1, preferably from 1:100 to 10:1.

Preferably, within the scope of the invention, R varies from 0.01 to 2.

It is interesting in certain cases to use ratios R of less than 1 in order to have partial hydrosilylation and obtain a reaction medium always including unreacted Si—H groups. The hydrosilylation method is then described as a partial one (this may also be referred to as a partial functionalization, the functionalization then corresponding to functionalization of an organosilicon compound i.e., to the reaction between Si—H groups of the organosilicon compounds and the compounds comprising at least one unsaturation).

The material (A) applied within the scope of the present invention has the advantage of having metal nanoparticles incorporated into the walls of the inorganic backbone. This localization of the metal nanoparticles in the walls allows stabilization of the metal which is not salted out in a homogenous phase in the reaction medium. This advantageously allows the possibility of being able to control the hydrosilylation reaction and to simply obtain compositions comprising partly functionalized organosilicon compounds (comprising unreacted SiH groups). This also gives the possibility of obtaining compositions comprising functionalized organosilicon compounds with different compounds (C).

Also in a particular embodiment, the method of the invention is a partial hydrosilylation method (P1) of organosilicon compounds (O) by a compound (C) comprising at least one unsaturation. In this particular embodiment of the method of the invention, R varies from 0.01 to 0.99.

In order to have this partial functionalization, it is also possible to introduce the compound (C) in excess relatively to the Si—H groups to suppress from the reaction medium the catalytic system, for example by filtration, after obtaining the desired functionalization level.

Also, the method according to the invention may comprise a step for removing the catalytic system after obtaining the desired conversion.

Such a partial functionalization method may be contemplated with difficulty, with the heterogeneous catalysts of the state of the art since the latter generally salts out platinum in a homogenous phase in the reaction medium, making the reaction media not very stable upon storage.

In another particular embodiment, the method of the invention gives the possibility of functionalizing with at least two compounds (C), the organosilicon compounds (O) according to a method (P2) comprising the following steps:

a) reacting the organosilicon compound (O) with a first compound (C), according to the method (P), R varying from 0.01 to 0.99; and b) reacting the organosilicon compound obtained in step a) with a second compound (C) different from the one applied in step a), according to the method (P), the ratio R of this step b) concerning the application of a second compound (C) varying from 0.01 to 1, the steps a) and b) being achieved in the presence of a catalyst as defined above.

The steps a) and b) may be applied several times within the scope of the method of the invention with different compounds (C). One skilled in the art may then, because of his/her general knowledge, determine the different ratios R to be applied, in the different steps and according to the different compounds (C) applied.

The methods (P), (P1) and (P2) according to the invention may be applied batch wise or continuously. Preferably, they are applied continuously.

When the method is applied continuously, the reactor is then selected from reactors known to one skilled in the art for conducting methods continuously. Notably, it is selected from fixed bed reactors, microreactors and tubular reactors.

Preferably, when the method is applied continuously, the material (A) is deposited on a substrate, for example metal beads which will be used in the case of a fixed bed reactor. The material (A) may also be deposited on the walls or on a constitutive element of the reactor.

Deposition of the material (A) on the suitable substrates may be accomplished with any method known to one skilled in the art and notably by the methods described in the publications of Perez et al. (Chemical Engineering Journal, 2010, 158, 325-322), Zhao et al. (Catalysis Today, 2009, 147, 215-219) and Wei et al. (Catalysis Today, 2009, 147, 66-70).

The present invention also relates to a device for applying a continuous method according to the invention, said device comprising a fixed bed reactor comprising the material (A) or comprising a reactor, at least one of the elements of which is covered with the material (A), notably with the methods described above. The reactor is preferably selected from reactors known to one skilled in the art for conducting methods continuously, notably this is a microreactor or a tubular reactor.

The invention also relates to the use of the material (A) as a hydrosilylation catalyst between an organosilicon compound and at least one compound comprising at least one unsaturation.

FIG. 1 represents a diagram of the material (A) according to the invention. The material (A) comprises walls (1) and pores (2). Metal nanoparticles (3) are incorporated into the walls (1). In this FIGURE ep represents the thickness of the walls and Dp the diameter of the pores.

The present application will now be described by means of non-limiting examples.

EXAMPLES

THF=Tetrahydrofurane

Example 1

Preparation of the Colloidal Suspension of Platinum

The method is as described in WO2010040926 and in the publication Boualleg et al., 2009, Chem. Mater, 21, 775-777.
100 mg (0.15 mmol) of $Pt(dba)_2$ (dba=dibenzylideneacetone) are placed in a glass reactor and under reduced pressure for 30 minutes at room temperature. 90 ml of THF are then added. 10 ml of THF containing 25 mg of 3-chloropropylsilane (0.15 mmol) are added at room temperature. The obtained solution is pressurized at 300 kPa (3 bars) of hydrogen with stirring for 12 hours.

A hydrophilicity test is conducted by placing the suspension of nanoparticles obtained in a container containing a biphasic water/heptane mixture, the water being located below the heptane in the container: the metal nanoparticles move into the aqueous phase and not into the heptane phase, which demonstrates their hydrophilicity.

Example 2

Preparation of the Catalyst

The method is as described in WO2010040926 and in the publication Boualleg et al., 2009, Chem. Mater, 21, 775-777.

In an Erlenmeyer of 150 ml, 0.5 g (86 µmol) of structuring surfactant Pluronic® 123 are added to 50 ml of distilled water containing 20 mg of NaF, under intense stirring. After obtaining a homogenous solution, 20 ml of a colloidal solution of hydrophilic platinum nanoparticles (24 µmol) prepared as indicated in Example 1, in a THF solvent, are added. The mixture is intensively stirred for 2 hours. The THF is then totally evaporated under reduced pressure. In a second Erlenmeyer 5 g (24 mmol) of TEOS are added to an aqueous solution of HCl (final pH of 1.5) and hydrolyzed for 3 hours. Both reaction mixtures are brought to 35° C. Both mixtures are then put into contact and the whole is finally stirred at 35° C. for 24 h. The grey-beige solid obtained is filtered, and then washed with twice 20 ml of water, ethanol, acetone and ether.

The obtained solid is then treated with the following method in order to remove the porogenic agent and the ligands:

1 g of the obtained material is placed in a glass tube of the pyrex type and calcined in dry air at 350° C. (temperature ramp: 2° C./min) for 10 hours in order to obtain the active catalyst.

Example 3

Description of the Catalysts Applied in the Examples

Various catalysts are applied in Examples 4 and 5 which follow. These catalysts are the following:
catalyst A: Pt/PS-DVB H2 160: platinum supported on polystyrene-divinylbenzene obtained from a precursor $Pt(acac)_2$, having been subject after preparation to a treatment with hydrogen at 160° C. This catalyst comprises 1% by weight of platinum.
catalyst B: Pt/PS-DVB H2 190: platinum supported on polystyrene-divinylbenzene obtained from a precursor $Pt(acac)_2$, having been subject after preparation to a treatment with hydrogen at 190° C. This catalyst comprises 1% by weight of platinum.
catalyst C: platinum supported on coal from Alfa Aesar (Pt/C Alfa Aesar). This catalyst comprises 1% by weight of platinum.
catalyst D to F: three different commercial batches of platinum supported on coal from Evonik (Pt/C Evonik AZ, Pt/C Evonik L11, Evonik L12). These catalysts comprise 3% by weight of plantinum.
catalyst G: platinum supported on non-porous silica treated in air at 320° C. ($Pt/SiO_2$ Air 320). This catalyst comprises 1% by weight of platinum.
catalyst H: platinum supported on non-porous silica treated with hydrogen at 450° C. ($Pt/SiO_2H_2$ 450). This catalyst comprises 1% by weight of platinum.
catalyst I: mesoporous silica comprising platinum nanoparticles in the pores (Pt/SBA (channels)). This catalyst comprises 0.3% by weight of platinum.
catalyst J: mesoporous silica comprising the platinum nanoparticles in the pores (Pt/SBA (channels)). The catalyst according to the invention obtained by the method described in Example 2. This catalyst comprises 0.3% by weight of platinum.

The catalysts A and B were synthesized according to the following method:

A solution of 220 mg of Pt $(acac)_2$ and 30 ml of $CHCl_3$ with 10 g of PS-DVB (300-800 µm, Aldrich, ref. 426989) is prepared. The mixture is left in a closed flask at room temperature for 24 h, the flask is then opened and the solvent evaporates for 24 h at room temperature.

The catalyst is then subject to the following treatment:

Catalyst A: 30 min under N2 at 25° C. and then 3 h under H2 at 160° C. (catalyst noted as Pt/PS-DVB 160).

Catalyst B: 30 min under N2 at 25° C. and then 5 h under H2 at 190° C. (catalyst noted as Pt/PS-DVB 190).

Catalysts C to F are available commercially.

The catalysts G and H were prepared according to the following method:

Silica (silicon oxide Alfa Aesar, catalyst support, low surface area, ref. 43861) is subject to the following treatment: Heating at 6° C./min up to 500° C. in air for 5 hours and then a secondary vacuum ($10^{-5}$ mbars) for 5 hours. The silica is then impregnated with a colloidal solution of Pt (30 mg of Pt all in all, i.e. 1% by weight) in THF with 1.45 ml THF/g of silica. The obtained catalyst is dried under an argon flow for 48 hours and is then subject to the following treatment: Catalyst G: calcination at 320° C. in air.

Catalyst H: treatment under hydrogen at 450° C.

Catalyst I was synthesized according to the method described in the publication Boualleg et al., 2009, Chem. Mater, 21, 775-777.

The catalyst J was synthesized according to Example 2.

Example 4

Hydrosilylation Reaction—Synthesis of a Polymethyloctylsiloxane

The following reaction was studied:

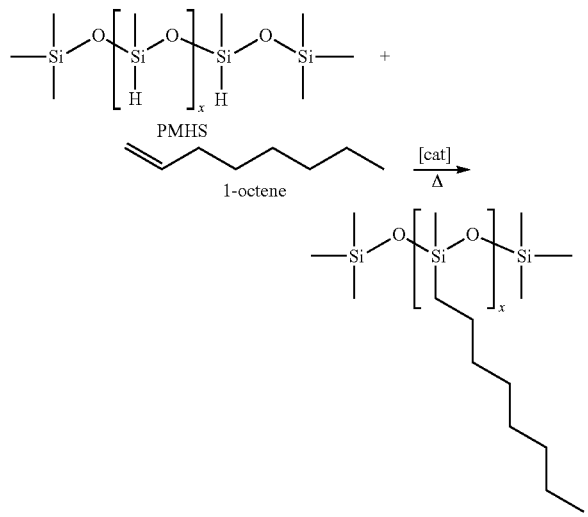

The experiments were conducted in a glass reactor of 300 ml equipped with a stirring shaft with tilted glass blades. Three counter blades in glass with a width of 5 mm were made against the walls. The reactor is placed in a thermostatic bath and the temperature may be adjusted to within a degree.

The reactor is equipped with a condenser, and a thermocouple placed in a glass glove finger within the reaction medium. Poly(methyl hydrogen siloxane) (also noted as PMHS) is introduced into the reactor by means of a syringe pump.

A poly(methyl hydrogen siloxane) (for which the concentration of [SiH] groups is 1.58 mol/100 g and which has a viscosity of 25 mPa·s) is added dropwise under an inert nitrogen atmosphere and at 70° C. to 1-octene (which is equivalent to a ratio $$R = \frac{\text{number of unsaturations of the } C \text{ compounds}}{\text{number of } SiH \text{ groups of the } O \text{ compounds}}$$

of about 1.3) in the presence of the catalysts of Example 3.

The reaction conditions of the tests according to the catalysts are summarized in the table below:

| Catalyst | 1-octene mass | PMHS mass | Catalyst mass (mg) | % Pt in the catalyst | Ppm of Pt in the medium |
|---|---|---|---|---|---|
| A: Pt/PS-DVB $H_2$ 160 | 39.4 | 17.3 | 62 | 1 | 10.9 |
| B: Pt/PS-DVB $H_2$ 190 | 42 | 16.9 | 71.7 | 1 | 12.2 |
| C: Pt/C Alfa Aesar 1% | 40.2 | 17.4 | 71.4 | 1 | 12.4 |
| D: Pt/C Evonik AZ | 41.8 | 16.9 | 13.9 | 3 | 7.1 |
| E: Pt/C Evonik L11 | 41.8 | 17.4 | 14.9 | 3 | 7.6 |
| F: Pt/C EvonikL12 | 41.6 | 17.3 | 16.9 | 3 | 8.6 |
| G: Pt/SiO$_2$ Air 320 | 40 | 17.4 | 38.5 | 1 | 6.7 |
| H: Pt/SiO$_2$ $H_2$ 450 | 40 | 17.5 | 35.2 | 1 | 6.1 |
| I: Pt/SBA (channels) | 40 | 17.2 | 110.5 | 0.3 | 5.8 |
| J: Pt/SBA (walls) | 40 | 17.1 | 103.6 | 0.3 | 5.4 |

These Examples show the case when the hydrosilylation reaction is conducted with an excess of compound (C) (R comprised between 1.3 and 1.4).

At the end of the pouring of PMHS, a first sample is taken and a gasometric dosage is achieved after filtration in order to evaluate the progress of the reaction at the end of the pouring via the consumption of the hydrogen siloxane functions. This gives the possibility of obtaining the TON (TON=the turnover number expresses the number of moles of converted SiH based on the initial number of moles of platinum) attained at the end of the pouring. These results are grouped in the column TON at the end of the pouring in the table below.

In parallel, a second sample of the reaction medium is taken. The sample reaction medium is filtered for removing the heterogeneous catalyst and again placed at 70° C. for 5 hours. The observed activity is then only due to the nanoparticles of Pt(0) which have been salted out into the reaction medium. This gives the possibility of obtaining the TON attained in a homogenous mode due to the platinum which will have been solubilized in the reaction medium and therefore demonstrating the salting out of platinum in the reaction medium. These results are grouped in the column TON additional 5 h (homogenous) in the table below.

Five hours after the end of the pouring of PMHS, a new sample of the reaction medium in the reactor is taken in order to follow the progression of the reaction and therefore the total TON over 5 hours. This total TON takes into account the TON at the end of the pouring, the TON due to salting out of the platinum in the reaction medium (i.e. the homogenous 5 h TON) and the TON due to the activity of the heterogeneous catalyst. It is thus possible to obtain the attained TON due to the heterogeneous catalyst (heterogeneous additional 5 h TON) by subtracting from the total TON, the TON at the end of the pouring and the homogeneous 5 h TON.

The results are expressed in a number of transformed SiH moles per initial mole of platinum:

| Catalyst | TON at the end of pouring | Additional 5 h TON (homogenous) | Total TON | Additional 5 h TON (heterogenous) |
|---|---|---|---|---|
| A | 15602 | 47352 | 62954 | 0 |
| B | 9584 | 49 | 14413 | 4780 |
| C | 6015 | 1788 | 29262 | 21459 |
| D | 42894 | 14238 | 99064 | 41933 |
| E | 35354 | 9906 | 93065 | 47805 |
| F | 31158 | 8391 | 79819 | 40270 |
| G | 46745 | 45705 | 99595 | 7145 |
| H | 13029 | 605 | 17391 | 3757 |
| I | 21229 | 55352 | 105028 | 28447 |
| J | 21287 | 4855 | 83281 | 57139 |

The results put forward that the Pt/PS-DVB catalysts having been subject to a heat treatment for avoiding leaching of the platinum nanoparticles certainly have low salting out of the Pt nanoparticles but however have a low catalytic activity.

The results also demonstrate that the Pt/C catalysts are not very repeatable. Indeed, according to the supplier or the batch, the Pt/C catalysts have quite different activities for the hydrosilylation reaction. On the contrary, the hydrosilylation reaction according to the invention was conducted with various batches of different catalysts of the invention and the results proved to be reproducible. Further, these results show that the Pt/C catalysts are at the origin of significant salting out of the Pt nanoparticles into the reaction medium.

The results obtained with $Pt/SiO_2$ treated at 320° C. demonstrate significant salting out of Pt into the medium. The same catalyst treated at 450° C. certainly allows reduction in the salting out of Pt, but the activity is found to be considerably limited.

The results obtained with Pt/SBA (channels) also show a very strong salting out of Pt into the medium.

As a comparison, the catalyst according to the invention advantageously has low salting out of Pt into the medium while having good activity. Indeed, for the catalyst of the invention, the activity after 5 hours of reaction is mainly due to the heterogeneous catalyst and not to the salted-out platinum in the reaction medium notably comparatively to the catalyst for which the nanoparticles are in the pores. This gives the possibility of showing that the Pt nanoparticles are trapped in the walls of the catalyst and are thus protected from leaching while remaining accessible to the reagents for allowing hydrosilylation.

These results also put forward that surprisingly, good hydrosilylation yields are obtained in spite of nanoparticles well integrated into the walls of the material (A), and therefore for one skilled in the art a priori difficult to access, even with a viscosity of the tested compound (O) about 15 times greater than that of water.

Example 5

Partial Hydrosilylation Reaction—Synthesis of a Poly(Methyl Hydrogen Siloxanes-Co-Methyloctylsiloxane)

This example shows the case of a hydrosilylation reaction conducted with a lack of compound (C).

A pre-mixture of poly(methyl hydrogen siloxane) (for which the [SiH] group concentration is of 1.58 mol/100 g and which has a viscosity of 25 mPa·s) and of 1-octene (which is equivalent to a ratio $$R = \frac{\text{number of unsaturations of the } C \text{ compounds}}{\text{number of SiH groups of the } O \text{ compounds}}$$

of 0.1) is added dropwise under a nitrogen atmosphere and at 70° C. to a solution of the heterogeneous J catalyst (catalyst according to the invention obtained by the method described in Example 2: Pt/SBA (walls)) (5 ppm of Pt by mass relatively to the reagents) diluted in toluene. After the end of the pouring, the reaction medium is maintained at 70° C. for 1 hour and then a sample is taken for $^1$H NMR analysis ($CDCl_3$) in order to control the progression of the reaction. When the reaction medium does not change over time, the latter is brought back to room temperature and then filtered in order to remove the heterogeneous J catalyst. Next the reaction medium is placed in vacuo (15 mbars) in order to remove the solvent (15 mbars) at 80° C. The finished product is then conditioned in air and stored at room temperature. The latter is stable over time without any gelling phenomenon at the surface.

Counter-Example 1

Partial Hydrosilylation Reaction—Synthesis of a Poly(Methyl Hydrogen Siloxane-Co-Methyloctylsiloxane)

This example shows the case of a hydrosilylation reaction conducted with a lack of compound (C).

A pre-mixture of polymethylhydrogen siloxane for which the [SiH] group concentration is 1.58 mol/100 g and which has a viscosity of 25 mPa·s) and of 1-octene (which is equivalent to a ratio $$R = \frac{\text{number of unsaturations of the } C \text{ compounds}}{\text{number of SiH groups of the } O \text{ compounds}}$$

of 0.1) is added dropwise under a nitrogen atmosphere and at 70° C. to a Karstedt platinum homogenous catalyst solution (5 ppm of Pt by mass relatively to the reagents) diluted in toluene. After the end of the pouring, the reaction medium is maintained at 70° C. for 1 hour and then a sample was taken for $^1$H NMR analysis ($CDCl_3$) in order to control progression of the reaction. When the reaction medium no longer changes, the latter is either devolatilized in vacuo (15 mbars) at 80° C. or treated beforehand with carbon black 2S (0.5% by mass/reaction medium) for 2 hours before being placed in vacuo for removing the solvent. The finished product is then conditioned in air and stored at room temperature. The latter is not stable. It rapidly changes in less than a quarter of an hour with the formation at the surface of a crust of a few cms which hardens over time and this whether the finished product has been treated with carbon black or not.

The invention claimed is:
1. A method (P) for hydrosilylating at least one compound (C) comprising at least one unsaturation in the presence of an organosilicon compound (O) comprising at least one hydrogen atom directly bound to a silicon atom and of a catalytic hydrosilylation system comprising a structured porous material (A) including pores and an inorganic backbone consisting of silicon oxide walls in which are contained metal nanoparticles.

2. The method according to claim 1, wherein the material (A) is in the form of a powder.

3. The method according to claim 2, wherein the material (A) as a powder is supported on a substrate.

4. The method according to claim 1, wherein the metal nanoparticles are platinum nanoparticles.

5. The method according to claim 1, wherein the material (A) has a double porosity with mesopores having a diameter from 2 to 50 nm and microporous channels, present in the walls of the material (A), having a diameter of less than 2 nm.

6. The method according to claim 1, wherein the material (A) has a BET specific surface area from 20 to 1,200 m²/g.

7. The method according to claim 1, wherein the metal nanoparticles have an average diameter from 1 to 10 nm.

8. The method according to claim 1, wherein the walls of the inorganic backbone of the material (A) have a thickness greater than or equal to 3 nm.

9. The method according to claim 1, wherein the inorganic backbone of the material (A) has a vermicular, cubic or hexagonal structure.

10. The method according to claim 1, wherein the compound (C) comprises one or several alkene functions and from 2 to 40 carbon atoms or one or several alkyn functions and from 2 to 40 carbon atoms.

11. The method according to claim 1, wherein the compound (C) is selected from the group consisting of:
$C_1$-$C_4$ alkyl acrylates and methacrylates;
acrylic acid or methacrylic acid;
acetylene;
alkenes;
non-conjugate dienes;
allyl alcohol;
allylamine;
allyl and glycidyl ether;
allyl and piperidine;
styrene;
1,2-epoxy-4-vinylcyclohexane;
chlorinated alkenes;
fluorinated alkenes;

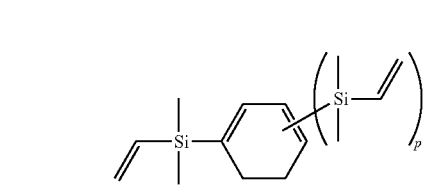

with p having the value 1 or 2;

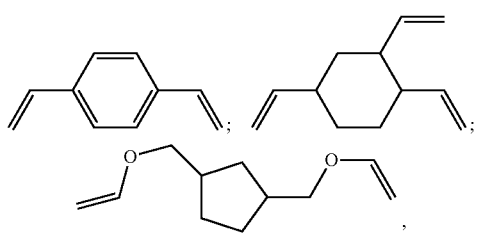

and mixtures thereof.

12. The method according to claim 1, wherein the compound (0) is selected from the group consisting of:
hydrogen silane compounds of formula (III):

wherein:
R represents independent of the others, a hydrogen atom; a halogen atom; an alkyl group optionally substituted with one or several aryl or cycloalkyl groups, with one or several halogen atoms and/or with one or several ketone functions; a cycloalkyl group optionally substituted with one or several alkyl groups and/or with one or several halogen atoms; or an aryl group optionally substituted with one or several alkyl groups and/or with one or several halogen atoms;
R' represents, independently of the others, an alkyl group optionally substituted with one or several aryl or cycloalkyl groups with one or several halogen atoms and/or with one ketone function; a cycloalkyl group optionally substituted with one or several alkyl groups and/or with one or several halogen atoms; or an aryl group optionally substituted with one or several alkyl groups and/or with one or several halogen atoms;
R" represents, independently of the others, a hydrogen atom; a halogen atom, preferably chlorine; an alkyl group optionally substituted with one or several aryl or cycloalkyl groups and/or with one or several halogen atoms; a cycloalkyl group optionally substituted with one or several alkyl groups and/or with one or several halogen atoms; or an aryl group optionally substituted with one or several alkyl groups and/or with one or several halogen atoms; and
m, n and o are integers of value 0, 1, 2 or 3, and m+n+o=3, R, R' and R" being either identical or different;
the polyorganosiloxanes comprising:
(i) at least one siloxyl unit of formula (IV)

wherein:
d=1 or 2,
e=0, 1 or 2
d+e=1, 2 or 3,
the symbol(s) $Z^3$, either identical or different, represent a monovalent hydrocarbon group notably having from 1 to carbon atoms optionally substituted with heteroatoms or radicals comprising heteroatoms,
(ii) optionally at least one siloxyl unit of formula (V)

wherein:
c=0, 1, 2 or 3;
the symbol(s) $Z^2$, either identical or different, represent a monovalent hydrocarbon group having from 1 to 30 carbon atoms optionally substituted with heteroatoms or with radicals comprising heteroatoms,
and mixtures thereof.

13. The method according to claim 1, wherein the molar ratio $$R = \frac{\text{number of unsaturations of the } C \text{ compounds}}{\text{number of } SiH \text{ groups of the } O \text{ compounds}}$$

varies from 0.01 to 2.

14. The method according to claim 1, wherein the amount of applied metal nanoparticles based on the total weight of the compounds (C) and (O) is from 1 to 50 ppm.

15. The method according to claim 1, wherein the molar ratio $$R = \frac{\text{number of unsaturations of the } C \text{ compounds}}{\text{number of } SiH \text{ groups of the } O \text{ compounds}}$$

varies from 0.01 to 0.99.

16. The method according to claim 1, comprising the following steps:
   a) reacting the organosilicon compound (0) with a first compound (C), according to the method (P), R varying from 0.01 to 0.99; and
   b) reacting the organosilicon compound obtained in step a) with a second compound (C) different from the one applied in step a), according to the method (P), the ratio R of this step b) concerning the application of a second compound (C) varying from 0.01 to 1,
   steps a) and b) being carried out in the presence of the catalytic system.

17. The method according to claim 1, wherein the method is carried out continuously.

18. The method according to claim 1, wherein the method is carried out at a temperature from 20 to 100° C.

19. A hydrosilylation catalytic system for reactions between an organosilicon compound (O) and a compound (C) comprising at least one unsaturation, comprising the material (A) according to claim 1.

* * * * *

UNITED STATES PATENT AND TRADEMARK OFFICE
CERTIFICATE OF CORRECTION

PATENT NO.         : 9,518,071 B2
APPLICATION NO.    : 14/653069
DATED              : December 13, 2016
INVENTOR(S)        : Chloe Thieuleux et al.

Page 1 of 1

It is certified that error appears in the above-identified patent and that said Letters Patent is hereby corrected as shown below:

On the Title Page

Item [71], Applicants delete:
"BLUESTAR SILICONES France SAS
(50 Percent Part Interest), Lyons (FR);
Universite Claude Bernard Lyon 1
(50 Percent Part Interest),
Villeurbanne (FR)"

And insert:
--Applicants:  BLUESTAR SILICONES France SAS,
              Lyons (FR); Universite Claude Bernard
              Lyon 1, Villeurbanne (FR)--

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*